United States Patent
Cohen et al.

(10) Patent No.: US 9,272,119 B2
(45) Date of Patent: Mar. 1, 2016

(54) METHODS FOR MANUFACTURING NON-PROLAPSING CATHETERS WITH LINERLESS TUBE

(71) Applicant: Covidien LP, Mansfield, MA (US)

(72) Inventors: Adam Cohen, Dallas, TX (US); Hao Wang, Beijing (CN)

(73) Assignee: Covidien LP, Mansfield, MA (US)

( * ) Notice: Subject to any disclaimer, the term of this patent is extended or adjusted under 35 U.S.C. 154(b) by 32 days.

(21) Appl. No.: 13/908,498

(22) Filed: Jun. 3, 2013

(65) Prior Publication Data

US 2014/0352871 A1   Dec. 4, 2014

(51) Int. Cl.
| | |
|---|---|
| *A61M 25/00* | (2006.01) |
| *B29C 53/58* | (2006.01) |
| *B29D 23/00* | (2006.01) |
| B29L 31/00 | (2006.01) |
| F16L 11/08 | (2006.01) |
| B29C 53/56 | (2006.01) |
| B29C 53/82 | (2006.01) |
| B29C 63/00 | (2006.01) |
| B29C 63/42 | (2006.01) |

(52) U.S. Cl.
CPC ....... *A61M 25/0012* (2013.01); *A61M 25/0009* (2013.01); *A61M 25/0013* (2013.01); *B29D 23/001* (2013.01); A61M 25/0051 (2013.01); B29C 53/566 (2013.01); B29C 53/822 (2013.01); B29C 63/0069 (2013.01); B29C 63/42 (2013.01); B29L 2031/7542 (2013.01); F16L 11/081 (2013.01)

(58) Field of Classification Search
CPC .......... A61M 25/005–25/0053; B29L 2031/7542–2031/7543; B29C 53/587

USPC ......... 156/143, 144, 168, 171–173, 184, 185, 156/187, 188, 190, 191, 194, 195; 604/526
See application file for complete search history.

(56) References Cited

U.S. PATENT DOCUMENTS

| | | | |
|---|---|---|---|
| 5,876,386 A | 3/1999 | Samson | |
| 5,951,539 A * | 9/1999 | Nita et al. | 604/526 |
| 6,669,886 B1 | 12/2003 | Willard | |
| 6,702,972 B1 | 3/2004 | Markle | |
| 8,142,415 B2 | 3/2012 | Warnock, Jr. et al. | |

(Continued)

FOREIGN PATENT DOCUMENTS

| | | |
|---|---|---|
| EP | 2371414 A1 | 10/2011 |
| WO | 9748437 A1 | 12/1997 |

OTHER PUBLICATIONS

International Search Report and Written Opinion from counterpart International Application No. PCT/US2014/034272, mailed Sep. 19, 2014, 18 pp.

(Continued)

*Primary Examiner* — Carson Gross
(74) *Attorney, Agent, or Firm* — Elizabeth A. O'Brien, Esq.

(57) ABSTRACT

A method for manufacturing a catheter member having at least one lumen is disclosed herein. The method includes, winding a sacrificial coil over a mandrel in a first direction and winding a reinforcement coil over the sacrificial coil in a second direction. A polymer is then laminated over the sacrificial coil and the reinforcement coil. After the polymer is laminated, the mandrel is removed and the sacrificial coil is removed to thereby form the catheter member having the lumen.

11 Claims, 13 Drawing Sheets

(56) References Cited

U.S. PATENT DOCUMENTS

| | | |
|---|---|---|
| 8,235,969 B2 | 8/2012 | Gregorich et al. |
| 2001/0010247 A1 | 8/2001 | Snow |
| 2006/0129179 A1 | 6/2006 | Weber et al. |
| 2006/0161135 A1 | 7/2006 | VanDerWoude |
| 2008/0312639 A1 | 12/2008 | Weber |
| 2010/0256603 A1 | 10/2010 | Lippert et al. |
| 2014/0083969 A1 * | 3/2014 | Porter ............... 216/7 |

OTHER PUBLICATIONS

International Preliminary Report on Patentability from counterpart International Application No. PCT/US2014/034272, mailed Dec. 17, 2015, 12 pp.

\* cited by examiner

METHODS FOR MANUFACTURING NON-PROLAPSING CATHETERS WITH LINERLESS TUBE

BACKGROUND

1. Technical Field

The present disclosure generally relates to catheters, and, in particular, relates to methods for manufacturing linerless non-prolapsing catheters.

2. Description of Related Art

Catheters are used in medical procedures to gain entry into a body cavity, duct, or vessel to allow drainage, administration of fluids or gases, access by surgical instrument, delivery of medical treatment devices, etc. Catheters may include a single tube or two or more tubes, e.g., coaxial catheters. such as balloon guide catheters. Coaxial catheters have at least an inner tube, an outer tube, and an annular lumen between the inner tube and the outer tube. In a coaxial catheter, the annular lumen may be reduced in cross-sectional area due to prolapse of the outer tube. A reduction in the cross-sectional area of the annular lumen may have an adverse affect on the flow rate of fluids through the annular lumen.

To reduce the risk of prolapse, the outer tube may incorporate a reinforcing structure such as a metal braid or coil to increase the radial strength of the outer tube. In braids, some of the wires are lifted over other wires when they cross. Because such wires are lifted, when constructing the catheter, molten polymer enters the space below the lifted wires thereby interlocking the braid within the polymer.

Sometimes braids may not be suitable for use in a catheter due to its effect on mechanical properties, or because the cross-sectional dimensions of the catheter do not allow for the braid to be included. In these instances, a coil may be used to reinforce the outer tube. In order to improve coil retention, a thin liner is included beneath the coil by winding the coil on the liner. As a result, the coil is disposed between the liner and the polymer after the catheter is constructed.

Due to such factors as dimensional constraints on outer tube diameter/crossing profile, inner tube diameter, and/or annular lumen width, it may be desirable to include a coil but impossible to include a liner. In such cases, there is a significant risk that the coil will delaminate from the tube during the catheter manufacturing process (e.g., during removal of the mandrel or insertion of the inner tube into the outer tube) or afterwards.

SUMMARY

The present disclosure is directed to a method for manufacturing a catheter member having a lumen. The method includes, winding a sacrificial coil over a mandrel in a first direction and winding a reinforcement coil over the sacrificial coil in a second direction. A polymer is then laminated over the sacrificial coil and the reinforcement coil. After the polymer is laminated, the mandrel is removed and the sacrificial coil is removed to thereby form the catheter member having the lumen.

In disclosed embodiments, subsequent to the step of removing the sacrificial coil, a second mandrel is inserted into the lumen. A heat shrink member is applied over the catheter member and the polymer is melted to fill at least one groove created by removing the sacrificial coil.

In disclosed embodiments, winding the sacrificial coil includes winding the sacrificial coil over the mandrel with a first pitch. In disclosed embodiments, winding the reinforcement coil includes winding the reinforcement coil over the sacrificial coil with a second pitch greater than the first pitch.

The present disclosure is also directed to a method for manufacturing a catheter member having an outer tube with a first lumen and an inner tube with a second lumen. The method includes laminating a liner over a mandrel and winding a reinforcement coil over the liner. A polymer is then laminated over the reinforcement coil and the liner to thereby form an outer tube having a first lumen. The method also includes removing the mandrel from the outer tube, inserting an inner tube having the second lumen into the first lumen, and removing the liner from the outer tube.

In disclosed embodiments, the step of laminating the liner over the mandrel includes stretching the liner over the mandrel and heating the liner.

In disclosed embodiments, the step of removing the mandrel from the outer tube includes stretching the mandrel and withdrawing the mandrel from one end of the outer tube.

In disclosed embodiments, the step of removing the liner includes placing the liner under longitudinal tension, separating the liner from the outer tube, and withdrawing the liner from one end of the outer tube.

The present disclosure is also directed to a method for manufacturing a catheter member having an annular lumen between an inner tube and an outer tube. The method includes disposing a spacer member over an inner tube, disposing a liner over the spacer member, and winding a reinforcement coil over the liner. A polymer is then laminated over the reinforcement coil and the liner to thereby form the outer tube disposed over the inner tube. The spacer member is removed thereby forming the annular lumen between the inner tube and the outer tube and the liner is removed from the annular lumen.

In disclosed embodiments, the step of removing the liner includes placing the liner under longitudinal tension, separating the liner from the outer tube, and withdrawing the liner from one end of the outer tube.

The present disclosure is also directed to a method for manufacturing a catheter member having at least one prolapse preventing member. The method includes providing a mandrel having at least one indentation and disposing a polymer layer over the mandrel. A heat shrink member is disposed over the polymer layer and the heat shrink member and the polymer layer are heated thereby causing the polymer layer to melt and flow into the indentation to form an outer tube with at least one prolapse preventing member extending radially inward toward a longitudinal axis of the outer tube of the catheter member.

In disclosed embodiments, the indentation is a groove extending along a longitudinal axis of the mandrel and the prolapse preventing member is a rib that extends along the longitudinal axis of the outer tube.

BRIEF DESCRIPTION OF THE DRAWINGS

Embodiments of the present disclosure will be readily appreciated by reference to the drawings wherein.

DETAILED DESCRIPTION

Figure 1A:
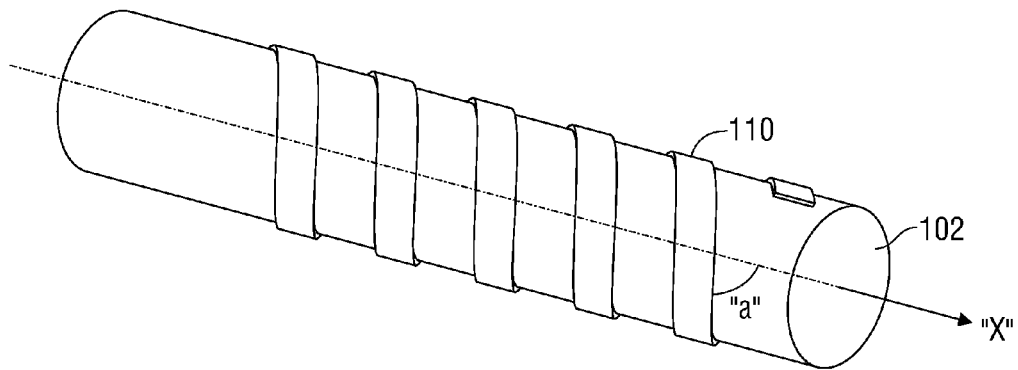
FIGS. 1A-1G illustrate a method of manufacturing a linerless non-prolapsing catheter in accordance with an embodiment of the present disclosure.

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

In the embodiments described herein, the catheter members may be manufactured by using a mandrel as a base. A mandrel is a cylindrical rod or shaft fabricated from, e.g., a polytetrafluoroethylene (PTFE). In other embodiments, the mandrel may be fabricated from silver plated copper or polyether ether ketone (PEEK). A wire, multiple wires, or a multi-stranded wire are wound around the mandrel to form a coil (e.g., a sacrificial coil or reinforcement coil). The wire(s) may be fabricated from stainless steel, nitinol, or cobalt chromium. The wires that form the coils may have a substantially rectangular cross-section, but may also have other cross-sections (e.g., circular or oval) that may be suitable for use with the embodiments described herein. In some embodiments, a liner may be disposed between the coils and the mandrel during the manufacturing process. The liner may be fabricated from PTFE or high-density polyethylene (HDPE).

A polymer tube may be disposed over the coils or directly over the mandrel. The polymer tube may be fabricated from a thermoplastic. In some embodiments, a heat shrink material is used during the manufacturing process. The heat shrink material may be composed of fluorinated ethylene propylene (FEP) or any other thermoplastic having heat shrink characteristics. In some embodiments, the catheter member may be formed on an inner tube instead of a mandrel or an inner tube may be inserted into the catheter member in a coaxial relationship with the outer tube after the mandrel is removed. The inner tube may be composed of PTFE or HDPE.

FIGS. 1A-1G illustrate a method for manufacturing a catheter member 100 in accordance with an embodiment of the present disclosure. As shown in FIG. 1A, a sacrificial coil 110 is wound over a mandrel 102. The sacrificial coil 110 is wound about the mandrel 102 at an angle "a" with respect to longitudinal axis "X" in a left-handed orientation or right-handed orientation.

Figure 1B:
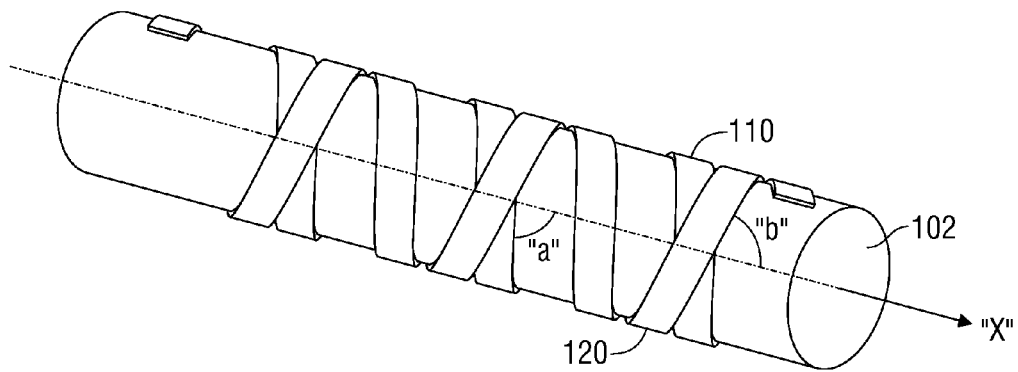

As shown in FIG. 1B, after the sacrificial coil 110 is wound about the mandrel 102, a reinforcement coil 120 is wound about the sacrificial coil 110 at an angle "b" with respect to longitudinal axis "X". The reinforcement coil 120 is wound in a different orientation than the sacrificial coil 110. For example, if the sacrificial coil 110 is wound about the mandrel 102 in a left-handed orientation, then the reinforcement coil 120 is wound about the sacrificial coil 110 in a right-handed orientation. The reinforcement coil 120 is wound about the sacrificial coil 110 with a light tension so that the turns of the reinforcement coil 120 remain substantially circular.

The pitch of the sacrificial coil 110 (as defined by angle "a") is less than the pitch of reinforcement coil 120 (as defined by angle "b"). The sacrificial coil 110 is wound with a small pitch in order to increase the number of locations at which the sacrificial coil 110 contacts the reinforcement coil 120 thereby lifting the reinforcement coil 120 above the mandrel 102 in these regions of contact. The pitch of the sacrificial coil 110 may be in the range of 250-125 wraps per inch (WPI). The pitch of the reinforcement coil 120 is greater than the pitch of the sacrificial coil, e.g, 100-25 WPI.

Figure 1C:
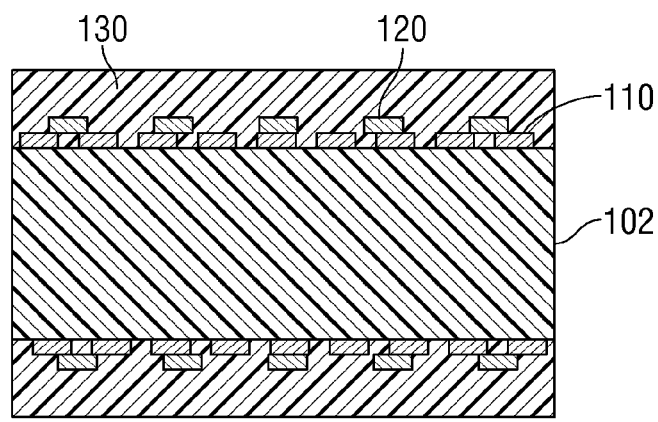
Figure 1D:
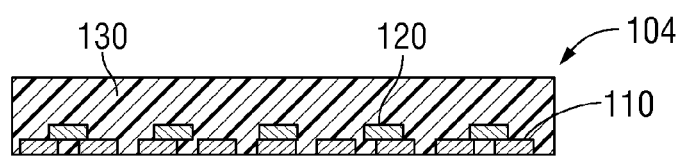
Figure 1D:
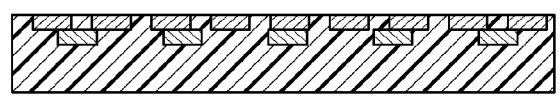
Figure 1E:
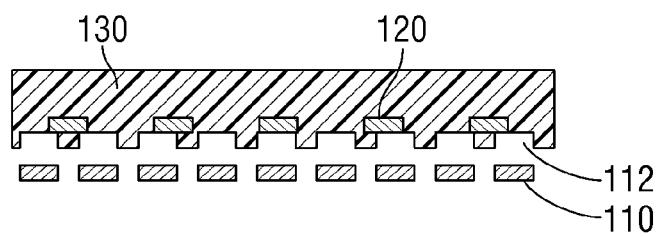
Figure 1E:
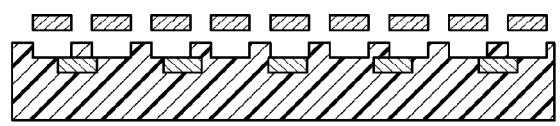

Once the reinforcement coil 120 is wound about sacrificial coil 110, a polymer tube 130 is laminated over mandrel 102, the sacrificial coil 110, and the reinforcement coil 120 as shown in FIG. 1C. The polymer tube 130 fills in the spaces between the turns of the sacrificial coil 110. As shown in FIG. 1D, after the polymer tube 130 is laminated, the mandrel 102 is removed resulting in the formation of the outer tube 104. The sacrificial coil 110 is delaminated from the outer tube 104 (as shown in FIG. 1E) leaving behind internal grooves 112 within the polymer tube 130. Thus, the catheter member 100 is formed with the reinforcement coil 120 embedded in the polymer tube 130 without the use of a liner. After the outer tube 104 is formed, an inner tube (not shown) may be inserted within the outer tube 104 and coupled via, e.g., a catheter hub to form a coaxial catheter member.

Figure 1F:
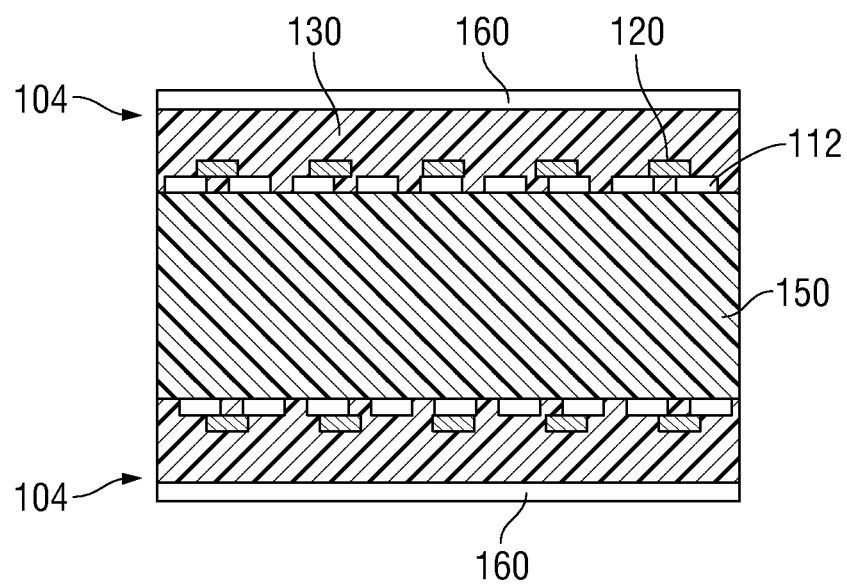
Figure 1G:
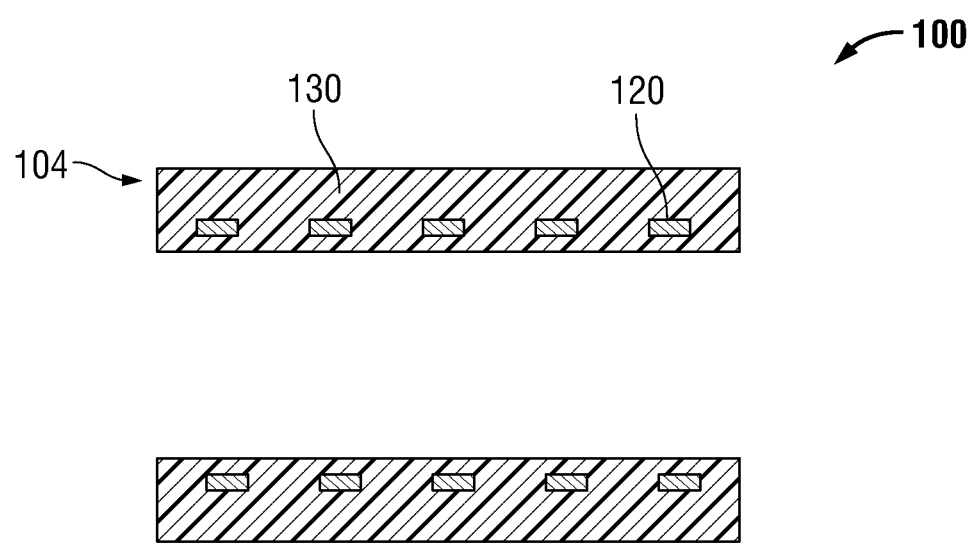

In some embodiments, after the sacrificial coil 110 is removed from the outer tube 104, a reflow procedure may be performed where the grooves 112 may be filled in with polymer from the polymer tube 130. As shown in FIG. 1F, a mandrel 150 is inserted into the outer tube 104 and a heat shrink 160 is disposed about the outer tube 104. Alternatively, the mandrel 102 may be reinserted into the outer tube 104 during the reflow procedure. Heat is then applied which causes the polymer of the polymer tube 130 to melt and the heat shrink 160 to shrink whereby the heat shrink 160 compresses the polymer tube 130 causing the melted or flowable polymer to fill the grooves 112. The catheter member 100 may also be manipulated during the melting process to facilitate flow of the polymer into the grooves 112. The mandrel 150 is removed and the reinforcement coil 120 is completely embedded in polymer 130 as shown in FIG. 1G. In the reflow procedure, the size of mandrel 150, heating parameters, dimensions of heat shrink 160, etc. are selected to embed the reinforcement coil 120 in the polymer 130 while maintaining the reinforcement coil 120 in spaced relation relative to the outer surface of the outer tube 104.

Figure 2A:
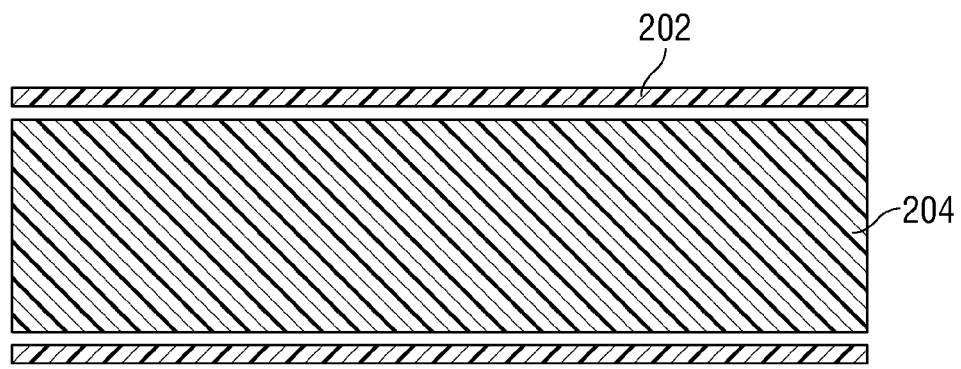
FIGS. 2A-2I illustrate a method of manufacturing a linerless non-prolapsing catheter in accordance with another embodiment of the present disclosure.
Figure 2B:
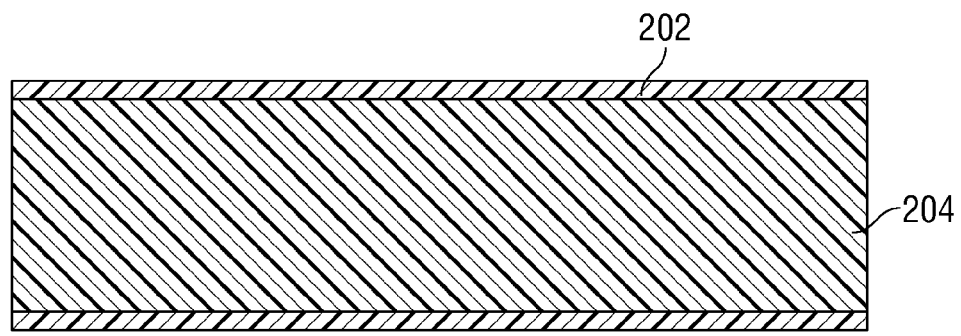
Figure 2C:
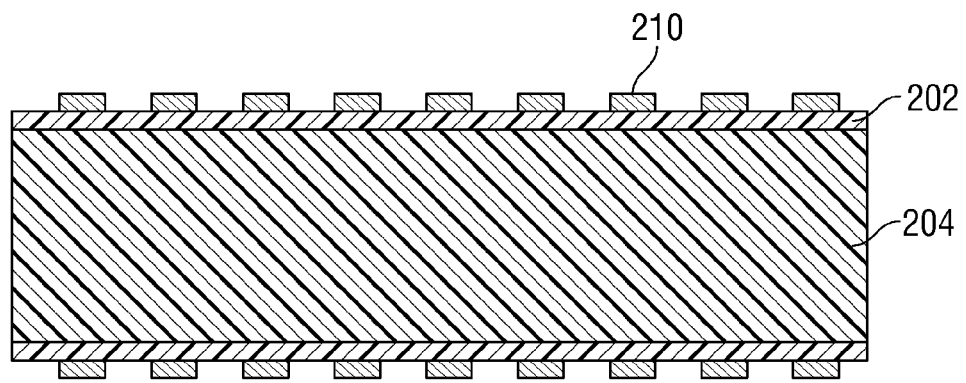

FIGS. 2A-2I illustrate a method for making a catheter member 200 in accordance with an embodiment of the present disclosure. As shown in FIG. 2A, a thin PTFE liner 202 is slipped over a mandrel 204. A PTFE liner 202 is stretched and heated to laminate the PTFE liner 202 onto the mandrel 204 as shown in FIG. 2B. A reinforcement coil 210 (FIG. 2C) is wound over the PTFE liner 202 in a left handed-orientation or a right-handed orientation with a pitch in the range of 100-25 WPI. The reinforcement coil 210 may be similar to reinforcement coil 120 previously discussed.

Figure 2D:
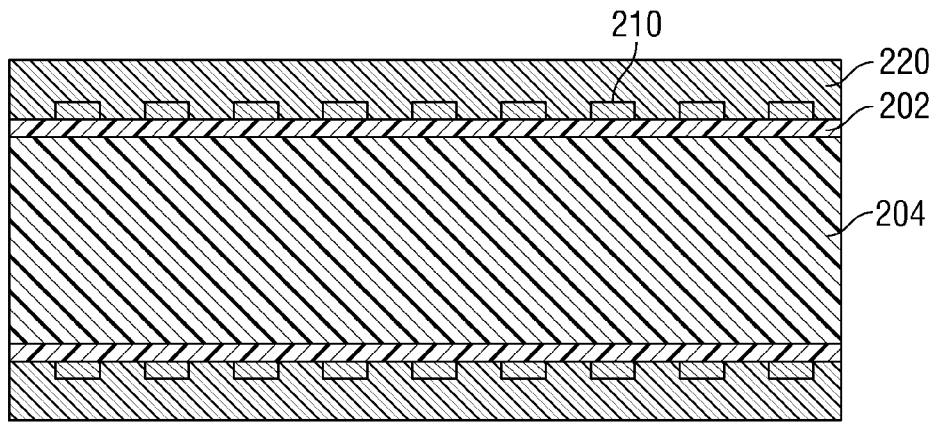
Figure 2E:
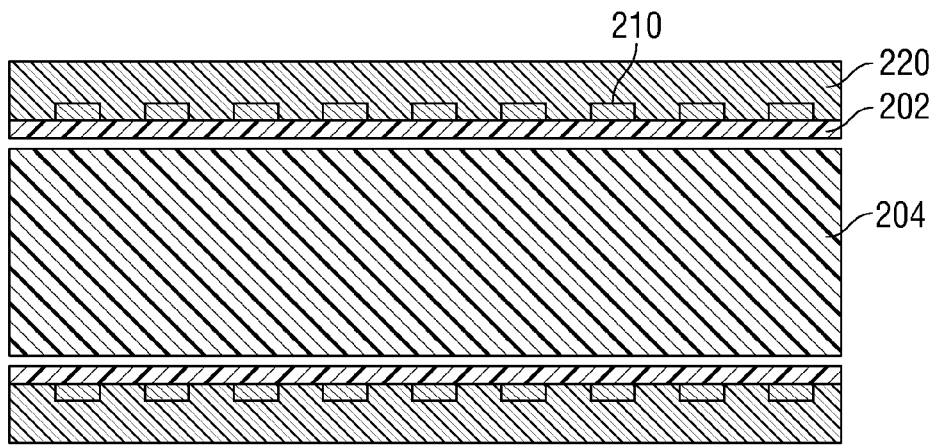
Figure 2F:
Figure 2F:
Figure 2F:
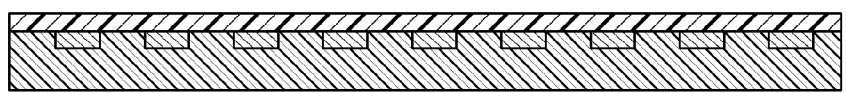
Figure 2G:
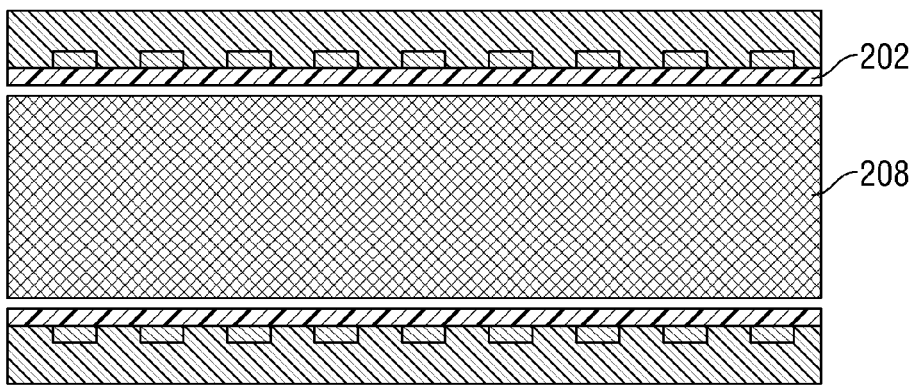

The polymer tube 220 is then laminated over the reinforcement coil 210 and the PTFE liner 202 as shown in FIG. 2D. The mandrel 204 is subsequently stretched by pulling both ends of the mandrel 204 in opposite directions. Pulling the ends of the mandrel 204 in opposite directions causes the mandrel 204 to delaminate from the PTFE liner 202 (FIG. 2E) which facilitates easy removal of the mandrel 204 leaving behind an outer tube 206 as shown in FIG. 2F.

Figure 2H:
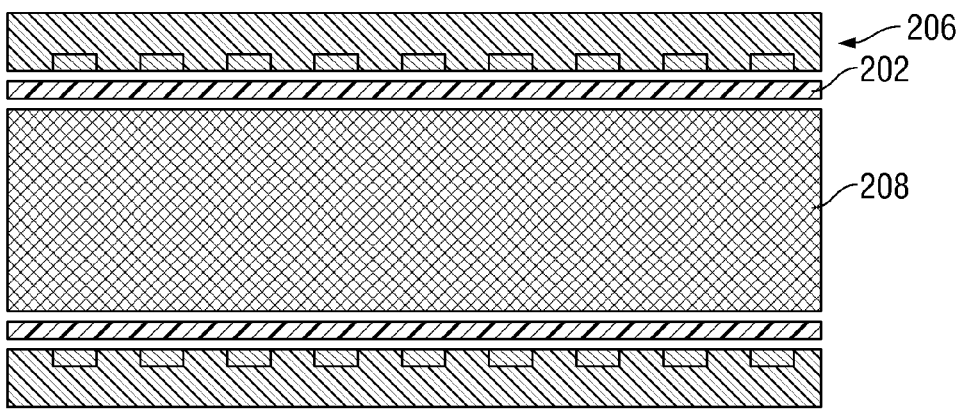
Figure 2I:
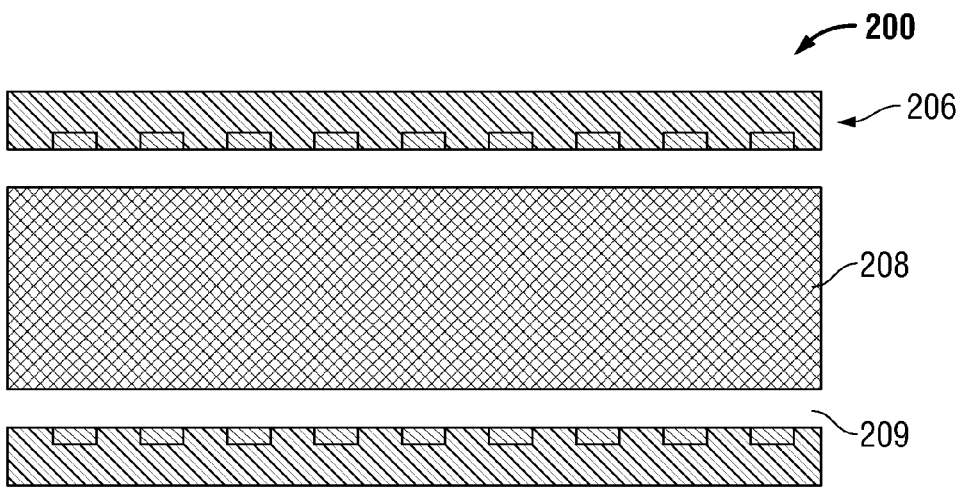

An inner tube 208 is introduced within the lumen 260 of the outer tube 206. (See FIG. 2G.) Once the inner tube 208 is in position, the PTFE liner 202 is stretched by pulling on both ends of the PTFE liner 202 thereby delaminating or separating the PTFE liner 202 from the outer tube 206 as shown in FIG. 2H. The PTFE liner 202 is then removed from one end of the lumen 260 thereby forming catheter member 200 with an outer tube 206, an inner tube 208 and annular lumen 209 disposed therebetween. (See FIG. 2I.)

Figure 3A:
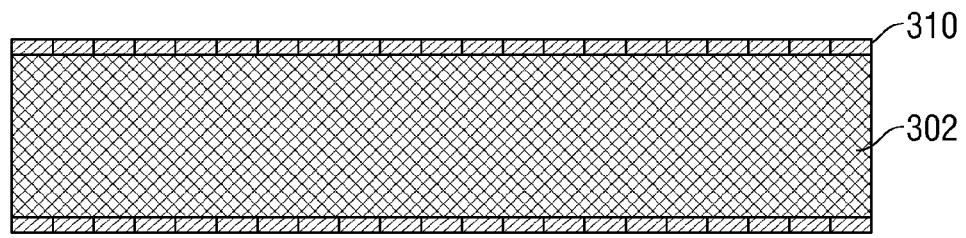
FIGS. 3A-3F illustrate a method of manufacturing a linerless non-prolapsing catheter in accordance with yet another embodiment of the present disclosure.
Figure 3B:
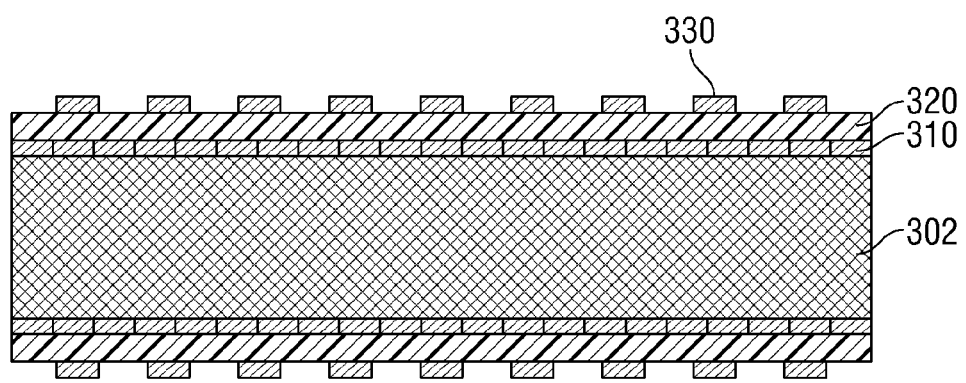

FIGS. 3A-3F illustrate a method for making a catheter member 300 in accordance with an embodiment of the present disclosure. As shown in FIG. 3A, a spacer member 310 is disposed about an inner tube 302. The spacer member 310 is a tightly wound coil with a relative small pitch, e.g., 1-3 times the width of the wire. The spacer member 310 may be fabricated from stainless steel, nitinol, or cobalt chromium. In other embodiments, the spacer member 310 may be a material (e.g., wax, a photoresist material, etc.) that can be removed by chemical dissolution and/or melting. As shown in FIG. 3B, a PTFE liner 320 is disposed about the spacer member 310 and a reinforcement coil 330 is wound over the PTFE liner 320 in a left handed-orientation or a right-handed orientation with a pitch in the range of 100-25 WPI.

Figure 3C:
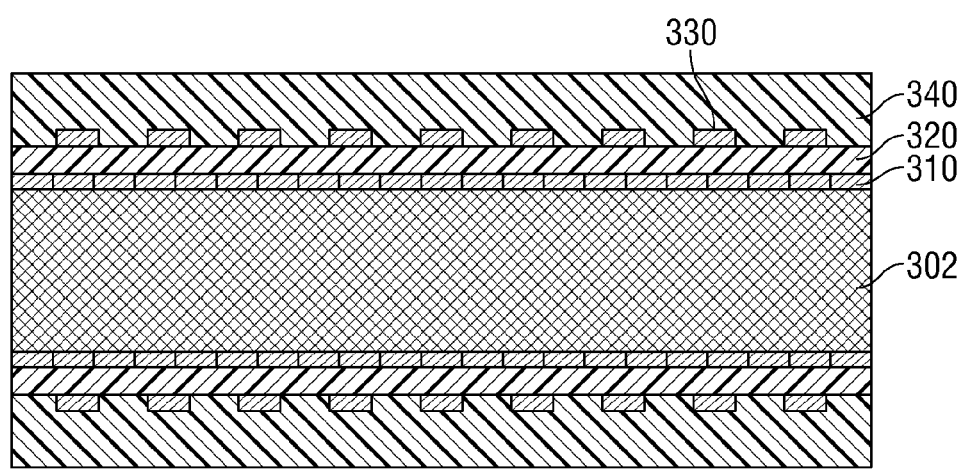
Figure 3D:
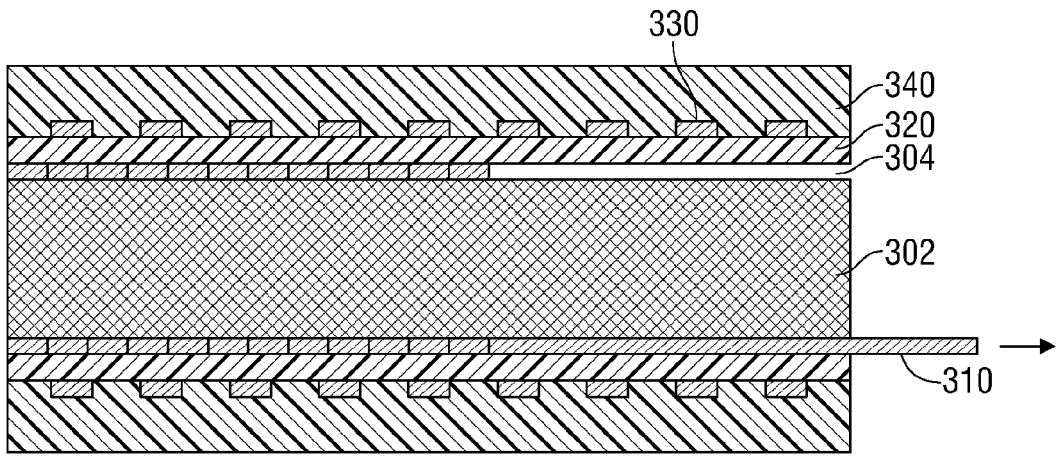

A polymer tube 340 is then laminated over the reinforcement coil 330 and the PTFE liner 320 as shown in FIG. 3C. Once the polymer tube 340 is laminated over the reinforcement coil 330 and the PTFE liner 320, the spacer member 310 is removed from an annular lumen 304 as shown in FIG. 3D. Specifically, if the spacer member 310 is a coiled wire, the wire is withdrawn from an end of the annular lumen 304 by pulling on an end of the wire thereby uncoiling the spacer member 310.

Figure 3E:
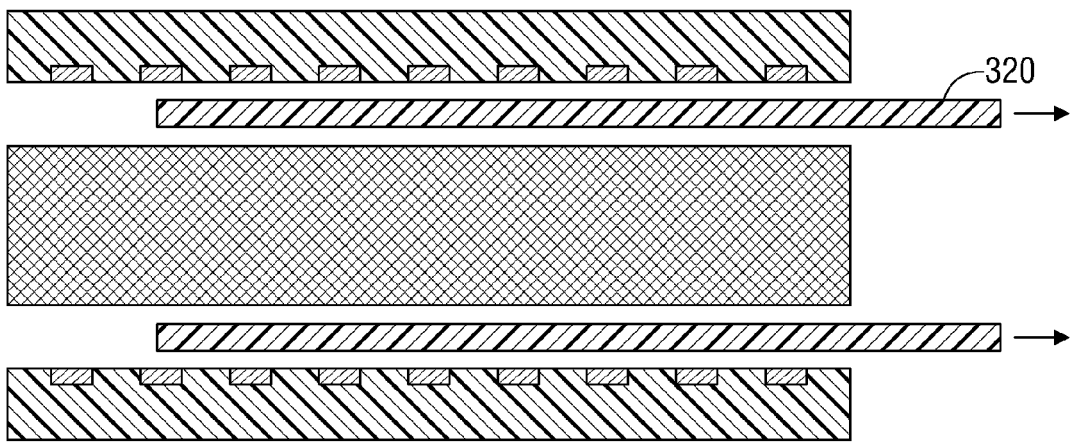
Figure 3F:
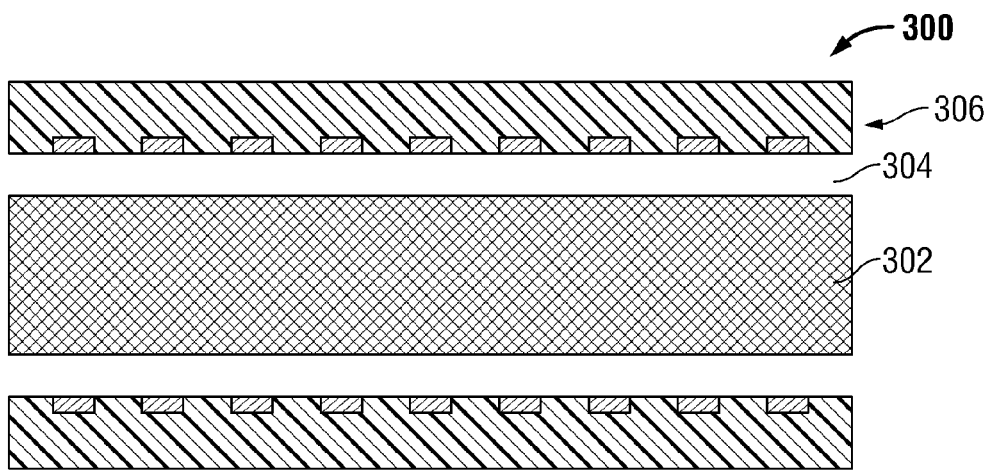

The PTFE liner 320 is stretched by pulling on both its ends to delaminate the PTFE liner 320 from the outer tube 306 as shown in FIG. 3E. The PTFE liner 320 is then removed from one end of the annular lumen 304 thereby forming a catheter member 300 with an outer tube 306, an inner tube 302 and an annular lumen 304. (See FIG. 3F.)

Figure 4A:
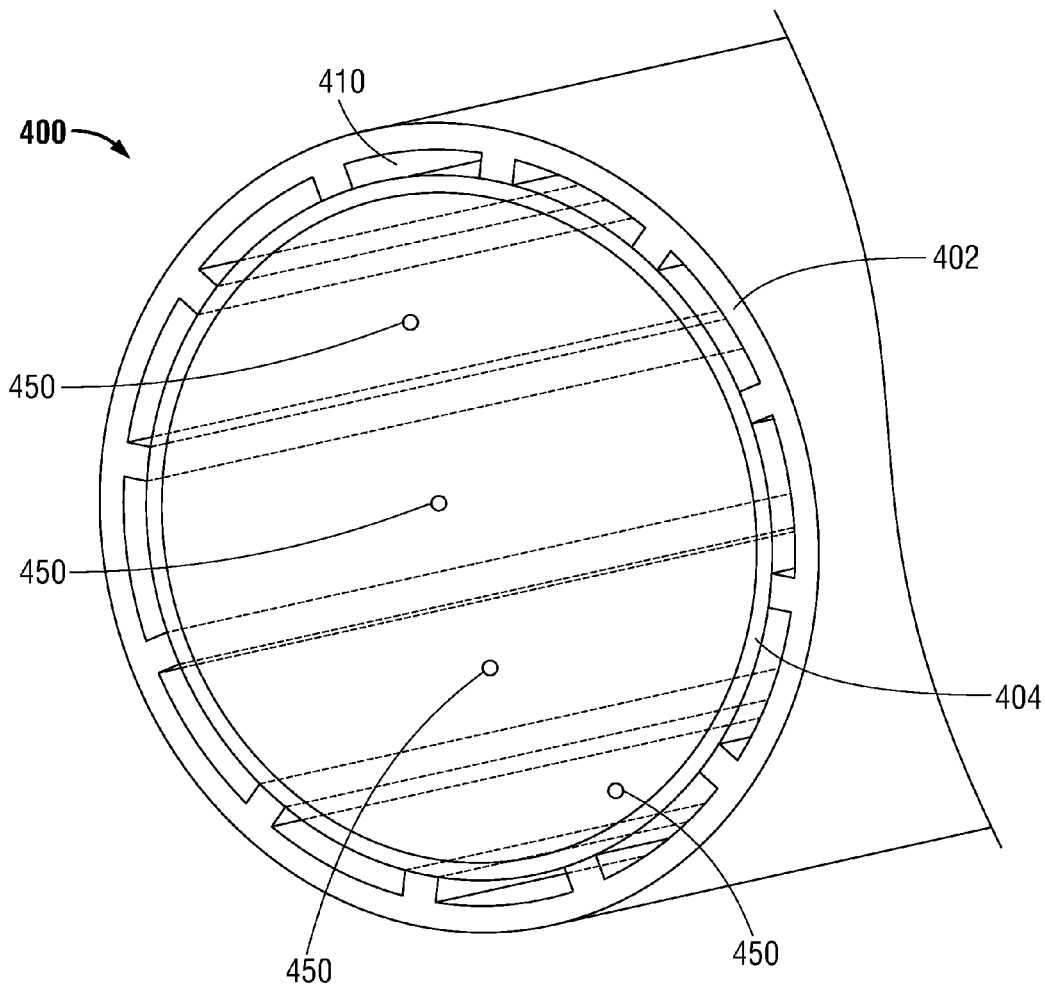
FIGS. 4A-4C illustrate a method of manufacturing a linerless non-prolapsing catheter in accordance with yet another embodiment of the present disclosure.

In some embodiments, the requirement of a coil to prevent prolapse of the outer tube may be obviated by the inclusion of prolapse-preventing structures located between the inner surface of the outer tube and the outer surface of the inner tube. For instance, as shown in FIG. 4A, a catheter member 400 includes a prolapse preventing member 410. The prolapse preventing member 410 may be independent, attached to the outer tube 402, the inner tube 404, or both the outer tube 402 and the inner tube 404. The prolapse preventing member 410 may be integrated into the outer tube 402, the inner tube 404, or both the outer tube 402 and the inner tube 404. The prolapse preventing member 410 may take the form of projections integrated with the inner surface of the outer tube. The projections may include bumps, bosses, ribs, or any other structures that may be suitable to prevent prolapse of outer tube 402.

Figure 4B:
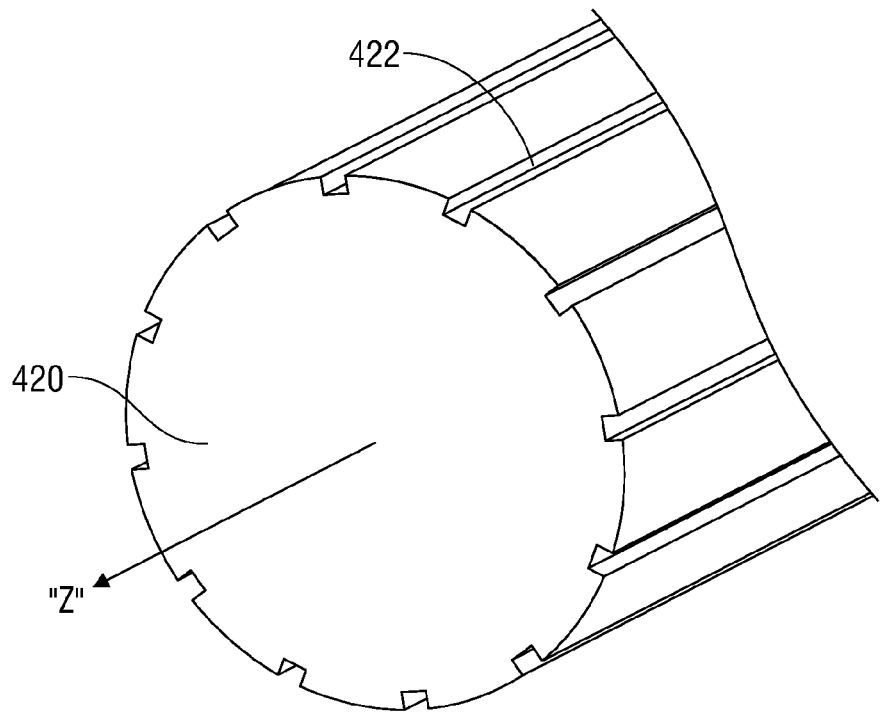

In a method for manufacturing the catheter member 400, a mandrel 420 having one or more indentations 422 formed along the longitudinal length of the mandrel 420 is provided. As shown in FIG. 4B, the indentations 422 are in the form of a groove that run parallel to the longitudinal axis "Z" of the mandrel 420. The indentations 422 have dimensions suitable for allowing softened and/or molten polymer from the outer tube 402 to flow into indentations 422.

Figure 4C:
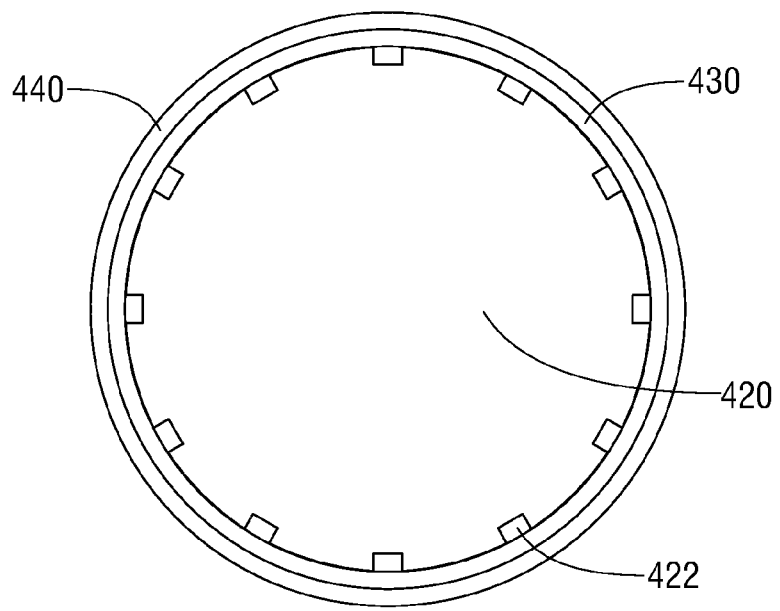

In the method, a polymer tube 430 is disposed over the mandrel 420 as shown in FIG. 4C. A heat shrink member 440 is then disposed over the polymer tube 430. Heat is then applied which causes the polymer of the polymer tube 430 to melt and heat shrink 440 to shrink thereby causing the polymer of the polymer tube 430 to fill the indentations 422. The mandrel 420 is removed and the inner tube 404 is inserted into the lumen 406 of the catheter member 400. The inner tube 404 is dimensioned to abut the prolapse preventing member 410. In some embodiments, if the catheter member 400 is being used as a balloon guide catheter, then balloon inflation holes 450 (FIG. 4A) may be created at multiple circumferential positions around the catheter member.

In some embodiments, a liner may be added at a distal end of the catheter member to prevent the coil from delaminating in a normally risky location. For instance, in balloon guide catheters, if a liner was disposed in the region of or proximal to the holes fluidly connecting the annular lumen to the balloon, the liner would restrict fluid flow. However, a liner may be added to the balloon guide catheter at the distal end of the catheter member without restricting fluid flow. FIGS. 5A-5J illustrate a method of manufacturing a catheter member 500 that has a liner disposed at a distal end 502 of catheter member 500.

Figure 5A:
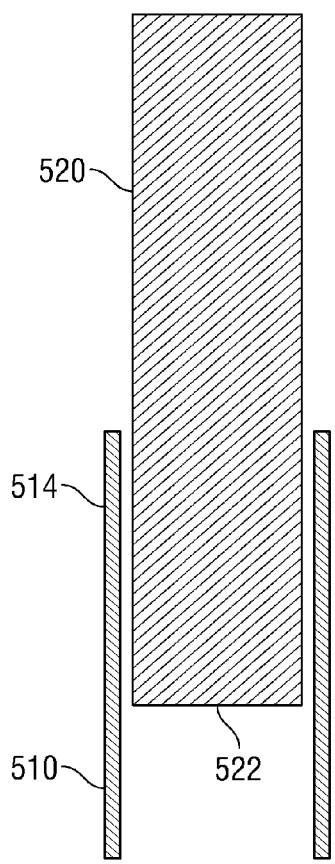
FIGS. 5A-5H illustrate a method of manufacturing a linerless non-prolapsing catheter in accordance with yet another embodiment of the present disclosure.
Figure 5B:
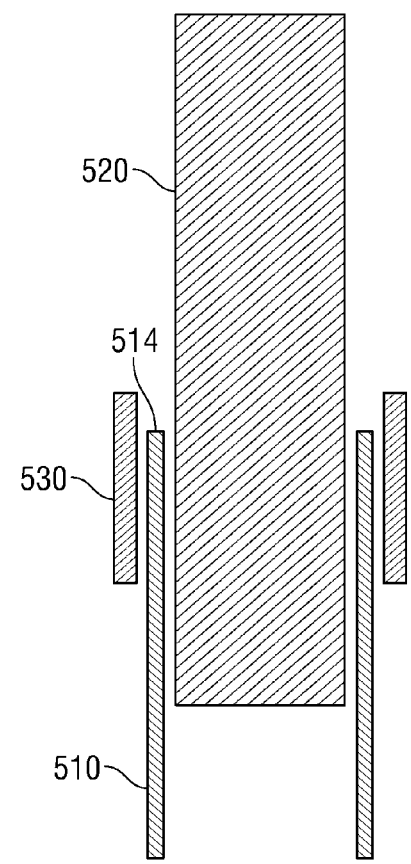
Figure 5E:
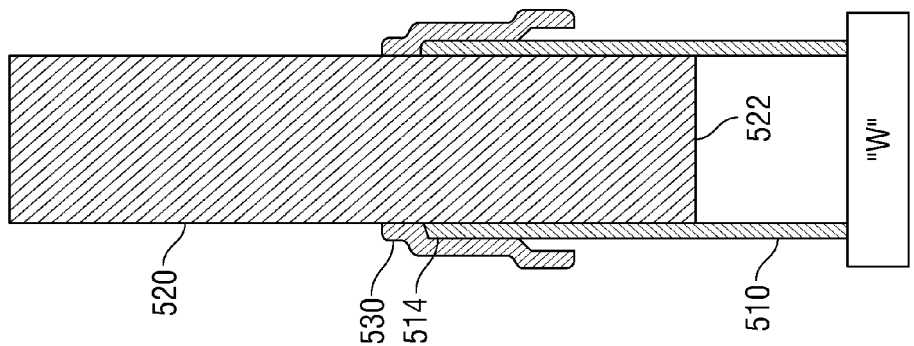
Figure 5D:
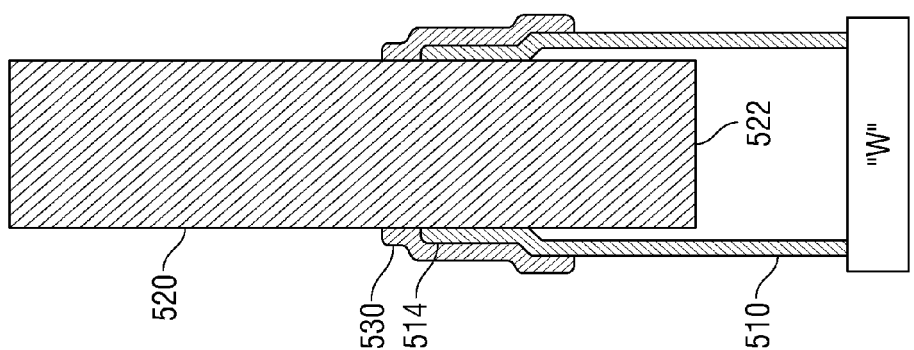
Figure 5C:
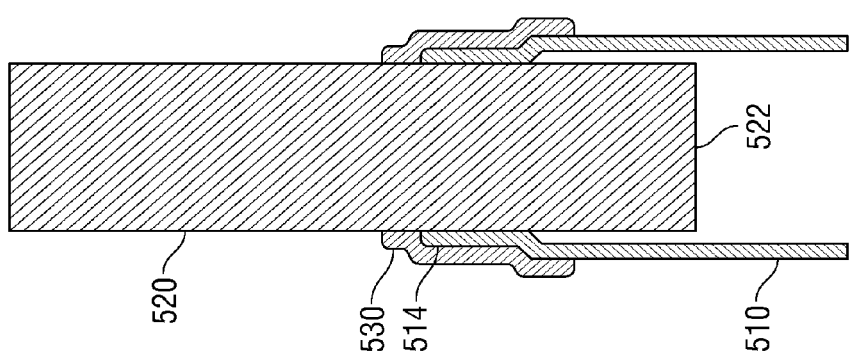
Figure 5H:
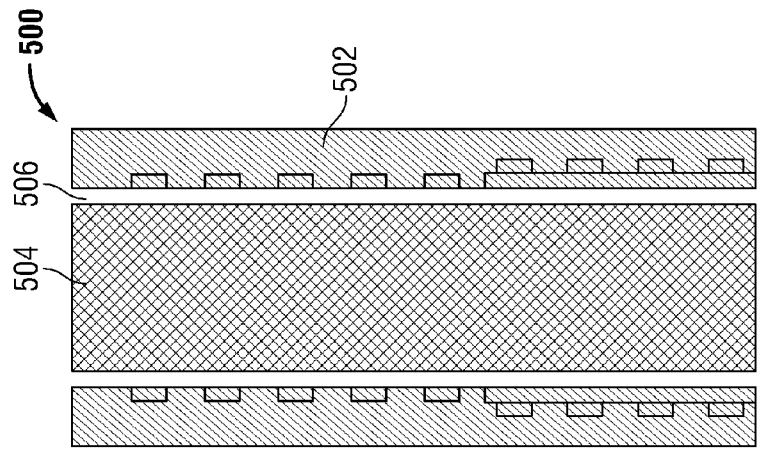
Figure 5G:
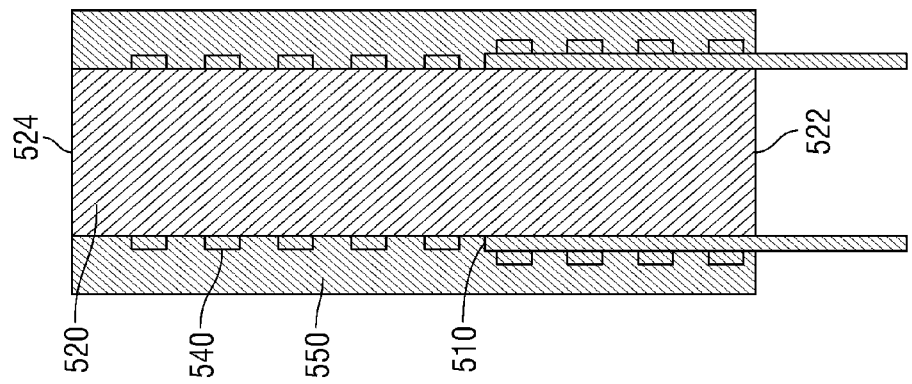
Figure 5F:
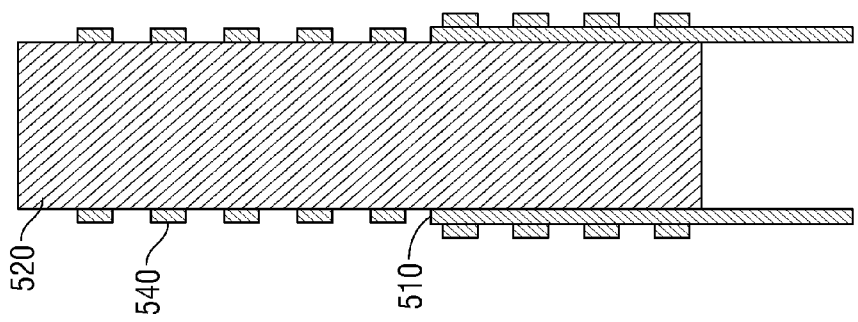

As shown in FIG. 5A, a proximal end 514 of the liner 510 is slipped over a distal end 522 of a mandrel 520. The liner 510 is fabricated from a material that can bond to the polymer that composes the outer tube 502 (FIG. 5G) and the polymer that composes the inner tube 504 (FIG. 5G). A heat shrink 530 (FIG. 5B) is slipped over the proximal end 514 of the liner 510. The proximal end 514 of the liner 510 is tacked onto the distal end 522 of the mandrel 520 by heating the heat shrink 530. (See FIG. 5C.) A weight "W" (FIG. 5D) is attached to a distal end 512 of the liner 510 to stretch the liner 510. The liner 510 is also heated while being stretched in order to laminate the proximal end 514 of the liner 510 to the distal end 522 of mandrel 520. (See FIG. 5E.)

After the liner 510 is laminated onto the mandrel 520, the heat shrink 530 and the weight "W" are removed and the proximal end 514 of the liner 510 may be trimmed if necessary. A reinforcement coil 540 is wound over the mandrel 520 and the liner 510 in a left-handed orientation or a right-handed orientation. (See FIG. 5F.) A polymer tube 550 (FIG. 5G) is laminated over the reinforcement coil 540, the liner 510, and the mandrel 520. The mandrel 520 is then stretched by pulling on the distal end 522 and the proximal end 524 of the mandrel 520 to delaminate the mandrel 520 from the outer tube 502. After the mandrel 520 is removed, the inner tube 504 is inserted into the lumen 506 of the outer tube 502 to form catheter member 500. (See FIG. 5H.)

The above description and the drawings are provided for the purpose of describing embodiments of the present disclosure and are not intended to limit the scope of the disclosure in any way. For example, while each embodiment of catheter members 100-500 illustrates either a single lumen catheter or a coaxial catheter, it is envisioned that multi-lumen catheters where the lumens are not in a coaxial relationship may also utilize the manufacturing principles embodied herein. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A method for manufacturing a catheter member having a lumen, the method comprising:
   winding a sacrificial coil over a mandrel in a first direction;
   winding a reinforcement coil over the sacrificial coil in a second direction;
   laminating a polymer over the sacrificial coil and the reinforcement coil;

removing the mandrel;

removing the sacrificial coil to thereby form the catheter member having the lumen; and filling at least one groove in the polymer created by removing the sacrificial coil.

2. The method according to claim 1, wherein filling the at least one groove in the polymer comprises:

inserting a second mandrel into the lumen;

applying a heat shrink member over the catheter member; and melting the polymer to fill the at least one groove created by removing the sacrificial coil.

3. The method according to claim 1, wherein the step of winding the sacrificial coil includes winding the sacrificial coil over the mandrel with a first pitch.

4. The method according to claim 3, wherein the step of winding the reinforcement coil includes winding the reinforcement coil over the sacrificial coil with a second pitch greater than the first pitch.

5. The method of claim 1, wherein at least one of the sacrificial coil or the reinforcement coil is fabricated from stainless steel.

6. The method of claim 1, wherein at least one of the sacrificial coil or the reinforcement coil is fabricated from nitinol.

7. The method of claim 1, wherein at least one of the sacrificial coil or the reinforcement coil is fabricated from cobalt chromium.

8. The method of claim 1, wherein the polymer is fabricated from a thermoplastic.

9. The method of claim 1, wherein laminating the polymer over the sacrificial coil and the reinforcement coil comprises laminating a polymer tube over the sacrificial coil and the reinforcement coil.

10. The method of claim 3, wherein the first pitch is in a range of 125 wraps per inch to 250 wraps per inch.

11. The method of claim 4, wherein the second pitch is in a range of 25 wraps per inch to 100 wraps per inch.

* * * * *